(12) United States Patent
Nocerino et al.

(10) Patent No.: US 6,444,628 B2
(45) Date of Patent: Sep. 3, 2002

(54) SHAMPOO COMPOSITIONS

(75) Inventors: Cecile Nocerino, Paris (FR); Ruby Loo Tan-Walker, Bath (GB)

(73) Assignee: Unilever Home & Personal Care USA, a division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/848,873

(22) Filed: May 4, 2001

(30) Foreign Application Priority Data

May 4, 2000 (GB) .............................. 0010806

(51) Int. Cl.[7] .............................. C11D 1/02; C11D 1/62; C11D 3/26

(52) U.S. Cl. .................. 510/124; 510/125; 510/127; 510/130; 510/137; 510/138; 510/158; 510/159; 510/504; 424/70.11; 424/70.19; 424/70.22; 424/70.28

(58) Field of Search .................. 510/124, 125, 510/127, 130, 137, 138, 158, 159, 504; 424/70.11, 70.19, 70.22, 70.28

(56) References Cited

U.S. PATENT DOCUMENTS

| 3,958,581 A | 5/1976 | Abegg et al. .................. 132/7 |
|---|---|---|
| 3,962,418 A | 6/1976 | Birkofer ...................... 424/70 |
| 5,151,210 A | 9/1992 | Steuri et al. .......... 252/174.017 |
| 5,194,639 A | 3/1993 | Connor et al. ................. 554/66 |
| 5,837,661 A * | 11/1998 | Evans et al. ................. 510/122 |
| 6,046,152 A * | 4/2000 | Vinson et al. ............... 510/428 |
| 6,221,817 B1 * | 4/2001 | Guskey et al. ............... 510/122 |
| 6,239,093 B1 * | 5/2001 | Foley et al. ................. 510/352 |
| 6,284,230 B1 * | 9/2001 | Sako et al. ............... 424/70.11 |
| 6,294,159 B1 * | 9/2001 | Reich et al. ............. 424/70.12 |
| 2001/0056048 A1 * | 12/2001 | Bertolosso et al. ......... 510/122 |

FOREIGN PATENT DOCUMENTS

| GB | 2177108 | * | 1/1987 |
| GB | 2177108 A | | 7/1989 |
| JP | 6293620 | | 10/1994 |
| WO | 92/06154 | | 4/1992 |

* cited by examiner

*Primary Examiner*—Gregory Delcotto
(74) *Attorney, Agent, or Firm*—Matthew Boxer

(57) ABSTRACT

An aqueous shampoo composition comprising, in addition to water an anionic cleansing surfactant, a cationic polymer, and a monoalkyl quaternary ammonium compound in which the alkyl chain length is C8 to C14.

4 Claims, No Drawings

SHAMPOO COMPOSITIONS

FIELD OF THE INVENTION

This invention relates o hair shampoo compositions which contain a combination of anionic surfactant, cationic polymer and a particular type of monoalkyl quaternary ammonium compound. The compositions provide conditioning benefits and enhanced removal of oily materials accumulated on the hair.

BACKGROUND AND PRIOR ART

Consumers oil hair both pre wash and post wash. Pre wash oiling is done as it is believed that oils nourish hair and protect it during the wash process. Post wash oiling is done for manageability and styling. The oiling habit is widely practised by around 800 million people across the Central Asia and Middle east region.

Hair becomes soiled and sticky due to its contact with dust and other particulate matter from the environment and, to a greater extent, from sebum secreted by the scalp. The build-up of the sebum causes the hair to have a dirty feel and unattractive appearance, a Situation requiring frequent hair shampooing, However, in the case of consumers who oil their hair, the problem arises that the oil on the hair may interfere with the action of the shampoo, both in terms of cleansing and conditioning.

There is therefore a need for a shampoo which can provide both conditioning benefits to the hair and enhanced removal of oily materials accumulated on the hair.

The present inventors have found that shampoo compositions which contain a combination of anionic surfactant, cationic polymer and a monoalkyl quaternary ammonium compound in which the alkyl chain length is C8 to C14 give superior conditioning and oil removal.

C8 to C14 monoalkyl quaternary ammonium compounds have been disclosed in the context of shampoos as follows:

GB 2177108 and U.S. Pat. No. 5,151,210 describe shampoos comprising anionic surfactant, silicone, suspending agent and a lauryl trimethyl quaternary ammonium salt. The shampoos are said to possess good stability and provide superior hair conditioning.

JP 06293620 describes a shampoo containing a lauryl trimethyl quaternary ammonium salt in conjunction with anionic and amphoteric surfactant. The shampoo is said to show good foamability and softening properties without damaging the hair.

None of the above documents disclose the inclusion of a cationic polymer in their formulations. Surprisingly, compositions of the invention exhibit improved deposition of cationic polymer onto the hair (and thus improved conditioning benefit) as well as enhancing oil removal from the hair.

SUMMARY OF THE INVENTION

The present invention provides an aqueous shampoo composition comprising, in addition to water:
 i) an anionic cleansing surfactant;
 ii) a cationic polymer, and
 iii) a monoalkyl quaternary ammonium compound in which the alkyl chain length is C8 to C14.

DETAILED DESCRIPTION AND PREFERRED EMBODIMENTS

Anionic Cleansing Surfactant

Shampoo compositions according to the invention comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate (n) EO, (where n ranges from 1 to 3).

Mixtures of any of the foregoing anionic cleansing surfactants may also be suitable.

The total amount of anionic cleansing surfactant in shampoo compositions of the invention is generally from 5 to 30%, preferably from 6 to 20%, more preferably from 8% to 18% by weight based on total weight of the shampoo composition.

Cationic Polymer

A cationic polymer is an essential ingredient in shampoo compositions of the invention.

The cationic polymer may be a homopolymer or be formed from two or more types of monomers. The molecular weight of the polymer will generally be between 5,000 and 10,000,000, typically at least 10,000 and preferably in the range 100,000 to about 2,000,000. The polymer will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl eaters, vinyl alcohol, maleic anhydride, propylene glycol and ethylene glycol.

The cationic amines can be primary, secondary or tertiary amines, depending upon the particular species and the pH of the composition, In general secondary and tertiary amines, especially tertiary, are preferred, Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
- copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
- copolymers of 1-vinyl-2-pyrrolidine and dimethylaminoethyl methacrylate, referred to in-the industry (CTFA) as Polyquaternium-11. This material is available commercially from GAF Corporation (Wayne, N.J., USA) under the GAFQUAT tradename (e.g., GAFQUAT 755N);
- cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl eaters of homo- and co-polymers of unsaturated carboxylic acids having from 3 to 5 carbon atoms, (as described in U.S. Pat. No. 4,009,256);
- cationic polyacrylamides(as described in WO95/22311).
- Other cationic polymers that can be used include cationic polysaccharide polymers, such as cationic cellulose derivatives, cationic starch derivatives, and cationic guar gum derivatives.
- Cationic polysaccharide polymers suitable for use in compositions of the invention include those of the formula:

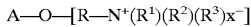

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl. arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. an described in U.S. Pat. No. 3,962,418), and copolymers of etherified cellulose-and starch (e.g. as described in U.S. Pat. No. 3,958,581).

A particularly suitable type of cationic polysaccharide polymer that can be used in a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17, having a high degree of substitution and a high viscosity, JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar gum derivatives.

Mixtures of any of the foregoing cationic polymers may also be suitable.

The cationic polymer may be present in an amount generally ranging from about 0.01 to about5% by weight of the total shampoo composition, preferably from 0.01 to 1% by weight. The enhanced deposition of cationic polymer observed with compositions of the invention means that the compositions can be formulated with a reduced level of cationic polymer than is customary. This has the benefit of improved sensory feel as well as; reduced cost since high levels of cationic polymer may sometimes be associated with an undesirable "Slimy" feel on the hair. A particularly preferred level of cationic polymer in compositions of the invention ranges from 0.05 to 0.5% by weight, since this delivers excellent sensory properties.

Monoalkyl Quaternary Ammonium Compound

Suitable monoalkyl quaternary ammonium compounds for use in compositions of the invention correspond to the general formula:

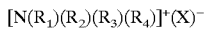

in which $R_1$ is a hydrocarbyl chain having 8 to 14 carbon atoms or a functionalised hydrocarbyl chain with 8 to 14 carbon atoms and containing ether, easter, amido or amino moieties present as substituents or as linkages in the radical chain, and $R_2$, $R_3$ and $R_4$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkyleater, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds for use in shampoos of the invention include:

(i) lauryl trimethylammonium chloride(available commercially as Arquad C35 ex-Akzo); cocodimethyl benzyl ammonium chloride (available commercially as Arquad DMCB-80 ex-Akzo)

(ii) compounds of the general formula:

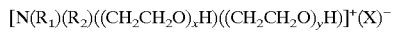

in which:
x+y is an integer from 2 to 20, and preferably less than 15;
$R_1$ is a hydrocarbyl chain having 8 to 14, preferably 12 to 14, moat preferably 12 carbon atoms or a functionalised hydrocarbyl chain with 8 to 14, preferably 12 to 14, most preferably 12 carbon atoms and containing ether, eater, amido or amino moieties present as substituents or as linkages in the radical chain;
$R_2$ is a $C_3$–$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such an PEO-2 cocomonium chloride (available commercially as Ethoquad C12 ex-Akzo Nobel); PE2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the general formula:

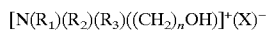

in which;
n is an integer from 1 to 4, preferably 2;
$R_1$ is a hydrocarbyl chain having 8 to 14, preferably 12 to 14, most preferably 12 carbon atoms;
$R_2$ and $R_3$ are independently selected from $C_1$–$C_3$ alkyl groups, and are preferably methyl, and
X is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing monoalkyl quaternary ammonium compounds may also be suitable.

For the avoidance of doubt, the monoalkyl quaternary ammonium compound of the invention does not encompass compounds comprising more than one quaternary ammonium group, e.g. di-quaternary ammonium compounds. Such multi-quaternary ammonium compounds can be included as additional components in the compositions of the invention. However, it is preferred that the compositions of the invention are substantially free of any multi-quaternary ammonium compounds.

The total amount of monoalkyl quaternary ammonium compound in shampoo compositions of the invention is generally from 0.05 to 6%, preferably from 0.1 to 4%, more preferably from 0.25% to 3% by weight based on total weight of the shampoo composition.

Optional Ingredients

Co-surfactants

The shampoo composition can optionally include co-surfactants, to help impart aesthetic, physical or cleansing properties to the composition.

A preferred example is an amphoteric or zwitterionic surfactant, which can be included in an amount ranging from 0 to about 8%, preferably from 1 to 4% by weight based on total weight of the shampoo composition.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0% to about 8% preferably from 2 to 5% by weight based on total weight of the shampoo composition.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G in a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{19}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

Other Optional Ingredient

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 54 by weight of the total composition.

The invention is further illustrated by way of the following non-limitative Examples, in which all percentages quoted are by weight based on total weight unless otherwise stated.

EXAMPLES

Example 1

Shampoo formulations were prepared having the ingredients an shown in the following Table:

| Ingredient | 1 control | 2 | 3 | 4 | 5 | 6 |
|---|---|---|---|---|---|---|
| Sodium Laureth Sulphate | 15 | 16 | 16 | 16 | 16 | 14 |
| Cocamidopropyl betaine | | 2 | 2 | 2 | 2 | 2 |
| Alkyl polyglucoside | | | | | | 2 |
| Cocomonoethanolamide | 2 | | | | | |
| Cocotrimonium chloride | | | 0.5 | | | |
| Laurylhydroxyethyl ammonium chloride | | | | 0.5 | | 0.5 |
| PEG-2 cocomonium chloride | | | | | 0.5 | |
| PEG-15 cocomonium chloride | | | | | 0.5 | |
| Jaguar C13S | 0.3 | 0.15 | 0.3 | 0.3 | 0.3 | 0.3 |
| Water, minors | | | | q.s. | | |

Formulation 1 is a control formulation and Formulations 2 to 6 are examples according to the invention.

Test Methodology

Hair switches were oiled with a commercial coconut hair oil. A fixed quantity of each prototype was applied onto the oiled hair switches. The product was then used in accordance with a normal procedure. On drying, the switches were assessed by semi-trained panellists on a number of attributes and scored (0–100).

Evaluation Results

The rating scores are shown in the Tables below for the attributes described;

| Test 1: Conditioning Attributes | | |
|---|---|---|
| | Ease of comb | Smoothness |
| Control | 41 | 43 |
| Example 2 | 58 ** | 53 * |

| Test 2: Conditioning Attributes | | | |
|---|---|---|---|
| | Ease of comb | Smoothness | Soft/Silky feel |
| Control | 44 | 42 | 40 |
| Example 3 | 59 ** | 61 ** | 64 *** |
| Example 6 | 72 *** | 67 *** | 62 *** |

| Test 3: Conditioning Attributes | | | |
|---|---|---|---|
| | Ease of comb | Smoothness | Soft/Silky feel |
| Control | 48 | 50 | 53 |
| Example 4 | 70 *** | 71 *** | 71 ** |
| Example 5 | 66 ** | 58 | 58 |

| Test 4: Clean and Shine Attributes | | | |
|---|---|---|---|
| | Clean appearance | Brightness | Contrast |
| Control | 22 | 20 | 26 |
| Example 2 | 40 *** | 50 *** | 35 ** |
| Example 3 | 38 ** | 30 | 38 ** |

\* $p < 0.05$; \*\* $p < 0.01$; \*\*\* $p < 0.001$

Example 2

Shampoo formulations were prepared having the ingredients as shown in the following Table:

| Ingredient | Control | Test |
|---|---|---|
| Sodium Laureth Sulphate | 15 | 15 |
| Cocomonoethanolamide | 2 | 2 |
| Cocotrimonium chloride | | 0.5 |
| Laurylhydroxyethyl ammonium chloride | | |
| Jaguar C13S | 0.3 | 0.3 |
| Water, minors | q.s. | q.s. |

The shampoo formulations were tested blind on a group of 300 consumers who regularly oiled their hair. After 2 weeks of use, the test product beat the control product specifically on oil removal and overall opinion ($p<0.05$).

What is claimed is:

1. An aqueous shampoo composition comprising, in addition to water:
   i) from about 5% to about 30% of an anionic cleansing surfactant;
   ii) from about 0.01% to about 5% of a cationic polymer, and
   iii) from about 0.05% to about 6% of a mon-long chain alkyl quaternary ammonium compound in which the alkyl chain length is C8 to C14.

2. A composition according to claim 1, in which said anionic cleansing surfactant is selected from the group consisting of sodium lauryl sulphate, sodium lauryl ether sulphate(n)EO, where n ranges from 1 to 3, ammonium lauryl sulphate and ammonium lauryl ether sulphate (n)EO, where n ranges from 1 to 3), and mixtures thereof.

3. A composition according to claim 1, in which said cationic polymer is selected from the group consisting of cationic cellulose and cationic guar gum derivatives, and mixtures thereof.

4. A composition according to claim 1, in which said mono-long chain alkyl quaternary ammonium compound is selected from the group consisting of lauryl trimethylammonium chloride, lauryldimethyl-hydroxyethylammonium chloride, and mixtures thereof.

\* \* \* \* \*